(12) United States Patent
Kornberg et al.

(10) Patent No.: US 11,732,381 B2
(45) Date of Patent: Aug. 22, 2023

(54) SYSTEMS AND METHODS TO IDENTIFY TRANSCRIPTION FACTOR ACTIVATION DOMAINS AND USES THEREOF

(71) Applicant: The Board of Trustees of the Leland Stanford Junior University, Stanford, CA (US)

(72) Inventors: Roger D. Kornberg, Atherton, CA (US); Adrian Sanborn, Redwood City, CA (US); Benjamin Yeh, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 43 days.

(21) Appl. No.: 17/300,935

(22) Filed: Dec. 15, 2021

(65) Prior Publication Data

US 2022/0186401 A1 Jun. 16, 2022

Related U.S. Application Data

(60) Provisional application No. 63/125,836, filed on Dec. 15, 2020.

(51) Int. Cl.
*C12Q 1/6811* (2018.01)
*C40B 30/04* (2006.01)
*G06N 3/02* (2006.01)
*C40B 40/10* (2006.01)

(52) U.S. Cl.
CPC ............ *C40B 30/04* (2013.01); *C12Q 1/6811* (2013.01); *C40B 40/10* (2013.01); *G06N 3/02* (2013.01)

(58) Field of Classification Search
None
See application file for complete search history.

(56) References Cited

FOREIGN PATENT DOCUMENTS

KR   100537636 B1   12/2005
WO   2012092439 A1   7/2012

OTHER PUBLICATIONS

Ansari et al., "Mechanisms of Mediator complex action in transcriptional activation", Cellular and Molecular Life Sciences, Aug. 2013, vol. 70, No. 15, pp. 2743-2756, published online Jan. 30, 2013, doi: 10.1007/s00018-013-1265-9.
Arnold et al., "A high-throughput method to identify transactivation domains within transcription factor sequences", The Embo Journal, 2018, vol. 37, e98896, pp. 1-13, published online Jul. 13, 2018, DOI 10.15252/embj.201798896.
Bailey, "DREME: motif discovery in transcription factor ChIP-seq data", Bioinformatics, 2011, vol. 27, No. 12, pp. 1653-1659, Advance Access publication May 4, 2011, doi:10.1093/bioinformatics/btr261.
Banani et al., "Compositional Control of Phase-Separated Cellular Bodies", Cell, Jul. 28, 2016, vol. 166, Issue 3, pp. 651-663, DOI: https://doi.org/10.1016/j.cell.2016.06.010.
Boija et al., "Transcription Factors Activate Genes through the Phase-Separation Capacity of Their Activation Domains", Cell, Dec. 13, 2018, vol. 175, pp. 1842-1855, https://doi.org/10.1016/j.cell.2018.10.042.
Bradner et al., "Transcriptional Addiction in Cancer", Cell, Feb. 9, 2017, vol. 168, Issue 4, pp. 629-643, DOI:https://doi.org/10.1016/j.cell.2016.12.013.
Brent et al., "A Eukaryotic Transcriptional Activator Bearing the DNA Specificity of a Prokaryotic Repressor", Cell, Dec. 1985, vol. 43. No. 2, pp. 729-736, doi: 10.1016/0092-8674(85)90246-6.
Brzovic et al., "The acidic transcription activator Gcn4 binds the mediator subunit Gal11/Med15 using a simple protein interface forming a fuzzy complex", Molecular Cell, Dec. 23, 2011, vol. 44, No. 6, pp. 942-953, doi: 10.1016/j.molcel.2011.11.008.
Ching et al., "Opportunities and obstacles for deep learning in biology and medicine", Journal of the Royal Society Interface, Apr. 2018, vol. 15, No. 141, 20170387, pp. 1-47, doi: 10.1098/rsif.2017.0387.
Chong et al., "Imaging dynamic and selective low-complexity domain interactions that control gene transcription", Science, Jul. 27, 2018, vol. 361, No. 6400, eaar2555, 25 pgs., published online Jun. 21, 2018, doi: 10.1126/science.aar2555.
Erijman et al., "A High-Throughput Screen for Transcription Activation Domains Reveals Their Sequence Features and Permits Prediction by Deep Learning", Molecular Cell, Jun. 4, 2020, vol. 78, Issue 5, pp. 890-902, first published May 15, 2020, DOI:https://doi.org/10.1016/j.molcel.2020.04.020.
Ferreira et al., "Mechanism of transcription factor recruitment by acidic activators", The Journal of Biological Chemistry, Jun. 10, 2005, vol. 280, No. 23, pp. 21779-21784, DOI:https://doi.org/10.1074/jbc.M502627200.
Govind et al., "Simultaneous Recruitment of Coactivators by Gcn4p Stimulates Multiple Steps of Transcription In Vivo", Molecular and Cellular Biology, Jul. 2005, vol. 25, No. 13, pp. 5626-5638, doi:10.1128/MCB.25.13.5626-5638.2005.
Graham et al., "Concentration-dependent exchange accelerates turnover of proteins bound to double-stranded DNA", Nucleic Acids Research, 2011, vol. 39, No. 6, pp. 2249-2259, published online Nov. 21, 2010, doi:10.1093/nar/gkq1140.
Hackett et al., "Learning causal networks using inducible transcription factors and transcriptome-wide time series", Molecular Systems Biology, 2020, vol. 16, e9174, 15 pgs., DOI 10.15252/msb.20199174.

(Continued)

*Primary Examiner* — Christopher M Gross
(74) *Attorney, Agent, or Firm* — KPPB LLP

(57) ABSTRACT

Embodiments herein describe systems and methods to identify transcription factor activation domains and uses thereof. Many embodiments obtain activation measurements of tiles or segments of known transcription factors in an organism. Further embodiments train a machine learning model, such as a convolutional neural network, to identify transcription factors and activation domains in other organisms of the same or different species. Such methods and systems can be used for industrial, medical, and research purposes.

20 Claims, 14 Drawing Sheets

(56) References Cited

OTHER PUBLICATIONS

Hahn et al., "Transcriptional regulation in *Saccharomyces cerevisiae*: transcription factor regulation and function, mechanisms of initiation, and roles of activators and coactivators", Genetics, Nov. 1, 2011, vol. 189, Issue 3, pp. 705-736, https://doi.org/10.1534/genetics.111.127019.

Herbig et al., "Mechanism of Mediator recruitment by tandem Gcn4 activation domains and three Gal11 activator-binding domains", Molecular Cell Biology, May 2010, vol. 30, No. 10, pp. 2376-2390, published online Mar. 22, 2010, doi:10.1128/MCB.01046-09.

Hope et al., "Functional Dissection of a Eukaryotic Transcriptional Activator Protein, GCN4 of Yeast", Cell, Sep. 12, 1986, vol. 46, pp. 885-894, DOI:https://doi.org/10.1016/0092-8674(86)90070-X.

Hope et al., "Structural and functional characterization of the short acidic transcriptional activation region of yeast GCN4 protein", Nature, Jun. 16, 1988, vol. 333, pp. 635-640, https://doi.org/10.1038/333635a0.

Jeronimo et al., "Kin28 regulates the transient association of Mediator with core promoters", Nature Structural & Molecular Biology, May 2014, vol. 21, No. 5, pp. 449-455, published online Apr. 6, 2014, doi: 10.1038/nsmb.2810.

Kagey et al., "Mediator and cohesin connect gene expression and chromatin architecture", Nature, Sep. 23, 2010, vol. 467, pp. 430-435, https://doi.org/10.1038/nature09380.

Kamar et al., "Facilitated dissociation of transcription factors from single DNA binding sites", PNAS Early Edition, 2017, vol. 114, pp. 1-7, www.pnas.org/doi/10..1073/pnas.1701884114.

Kelley et al., "Basset: learning the regulatory code of the accessible genome with deep convolutional neural networks", Genome Research, May 3, 2016, vol. 26, pp. 990-999.

Knoll et al., "Role of the pre-initiation complex in Mediator recruitment and dynamics", eLife, 2018, vol. 7, e39633, 23 pgs., DOI: https://doi.org/10.7554/eLife.39633.

Kornberg, "Mediator and the mechanism of transcriptional activation", Trends in Biochemical Sciences, May 1, 2005, vol. 30, No. 5, pp. 235-239, doi: 10.1016/j.tibs.2005.03.011.

Layer et al., "Direct transactivator-transcription factor IID (TFIID) contacts drive yeast ribosomal protein gene transcription", Journal of Biological Chemistry, May 14, 2010, vol. 285, No. 20, pp. 15489-15499, published online Feb. 26, 2010, doi: 10.1074/jbc.M110.104810.

Liu et al., "Fungal mediator tail subunits contain classical transcriptional activation domains", Molecular Cellular Biology, Apr. 2015, vol. 35, pp. 1363-1375, DOI: https://doi.org/10.1128/MCB.01508-14.

Mcisaac et al., "Synthetic gene expression perturbation systems with rapid, tunable, single-gene specificity in yeast", Nucleic Acids Research, 2012, pp. 1-10, Advance Access published Dec. 24, 2012, DOI:10.1093/nar/gks1313.

Oates et al., "D2P2: Database of Disordered Protein Predictions", Nucleic Acids Research, 2012, Advance Access published Nov. 29, 2012, pp. 1-9, DOI:10.1093/nar/gks1226.

Piskacek et al., "Nine-amino-acid transactivation domain: establishment and prediction utilities", Genomics, Jun. 2007, vol. 89, No. 6, pp. 756-768, published online Apr. 30, 2007, doi: 10.1016/j.ygeno.2007.02.003.

Ptashne et al., "Transcriptional activation by recruitment", Nature, Apr. 10, 1997, vol. 386. No. 6625, pp. 569-577, doi: 10.1038/386569a0.

Ravarani et al., "High-throughput discovery of functional disordered regions investigation of transactivation domains", Molecular Systems Biology, May 14, 2018, vol. 14, No. 5, e8190, 14 pgs., doi: 10.15252/msb.20188190.

Raveh et al., "Rosetta FlexPepDock ab-initio: simultaneous folding, docking and refinement of peptides onto their receptors", PLoS One, Apr. 29, 2011, vol. 6, No. 4, e18934, 10 pgs., doi: 10.1371/journal.pone.0018934.

Robinson et al., "Structure of a Complete Mediator-RNA Polymerase II Pre-Initiation Complex", Cell, 2016, vol. 166, pp. 1411-1422, http://dx.doi.org/10.1016/j.cell.2016.08.050.

Sabari et al., "Coactivator condensation at super-enhancers links phase separation and gene control", Science, Jul. 27, 2018, vol. 361, No. 6400, eaar3958, 24 pgs., published online Jun. 21, 2018, doi: 10.1126/science.aar3958.

Shrinivas et al., "Enhancer Features that Drive Formation of Transcriptional Condensates", Molecular Cell, Aug. 8, 2019, vol. 75, No. 3, pp. 549-561.e7, doi: 10.1016/j.molcel.2019.07.009.

Spitz et al., "Transcription factors: from enhancer binding to developmental control", Nature Reviews Genetics, Sep. 2012, vol. 13, pp. 613-626, published online Aug. 7, 2012, doi:10.1038/nrg3207.

Staller et al., "A High-Throughput Mutational Scan of an Intrinsically Disordered Acidic Transcriptional Activation Domain", Cell Systems, Apr. 25, 2018, vol. 6, No. 4, pp. 444-455.e6, published online Mar. 7, 2018, doi: 10.1016/j.cels.2018.01.015.

Sugase et al., "Mechanism of coupled folding and binding of an intrinsically disordered protein", Nature, Jul. 2007, vol. 447, No. 7147, pp. 1021-1025, DOI:10.1038/nature05858.

Thakur et al., "A nuclear receptor-like pathway regulating multidrug resistance in fungi", Nature, Apr. 3, 2008, vol. 452, No. 7187, pp. 604-609, doi: 10.1038/nature06836.

Titz et al., "Transcriptional activators in yeast", Nucleic Acids Research, 2006, vol. 34, No. 3, pp. 955-967, published online Feb. 7, 2006, doi: 10.1093/nar/gkj493.

Tompa et al., "Fuzzy complexes: polymorphism and structural disorder in protein-protein interactions", Trends in Biochemical Sciences, vol. 33, No. 1, pp. 2-8, available online Nov. 28, 2007, doi:10.1016/j.tibs.2007.10.003.

Tuttle et al., "Gcn4-Mediator Specificity Is Mediated by a Large and Dynamic Fuzzy Protein-Protein Complex", Cell Reports, Mar. 20, 2018, vol. 22, No. 12, pp. 3251-3264, doi: 10.1016/j.celrep.2018.02.097.

Tycko et al., "High-Throughput Discovery and Characterization of Human Transcriptional Effectors", Cell, Dec. 23, 2020, vol. 183, No. 7, pp. 2020-2035.e16, published online Dec. 5, 2020, doi: 10.1016/j.cell.2020.11.024.

Wang et al., "Proteolytic Instability and the Action of Nonclassical Transcriptional Activators", Current Biology, May 11, 2010, vol. 20, No. 9, pp. 868-871, published online Apr. 22, 2010, doi: 10.1016/j.cub.2010.03.029.

Warfield et al., "A sequence-specific transcription activator motif and powerful synthetic variants that bind Mediator using a fuzzy protein interface", PNAS, Aug. 25, 2014, vol. 111, No. 34. pp. E3506-E3513, published online Aug. 13, 2014. doi: 10.1073/pnas.1412088111.

Wimley et al., "Experimentally determined hydrophobicity scale for proteins at membrane interfaces", Nat Struct Biology, Oct. 1996, vol. 3, No. 10, pp. 842-848, doi: 10.1038/nsb1096-842.

Wong et al., "TFIIH phosphorylation of the Pol II CTD stimulates mediator dissociation from the preinitiation complex and promoter escape", Molecular Cell, May 22, 2014, vol. 54, No. 4, pp. 601-612, published online Apr. 17, 2014. doi: 10.1016/j.molcel.2014.03.024.

Wright et al., "The negative charge of Glu-111 is required to activate the cleavage center of EcoRI endonuclease", Journal of Biological Chemistry, Jul. 15, 1989, vol. 264, No. 20, pp. 11816-11821.

Wright et al., "TAF4 nucleates a core subcomplex of TFIID and mediates activated transcription from a TATA-less promoter", PNAS, Aug. 15, 2006, vol. 103, No. 33, pp. 12347-12352, www.pnas.orgcgidoi10.1073pnas.0605499103.

Zhang et al., "A Triad of Subunits from the Gal11/Tail Domain of Srb Mediator Is an In Vivo Target of Transcriptional Activator Gcn4p", Molecular and Cellular Biology, Sep. 2004, vol. 24, No. 15, pp. 6871-6886, DOI:10.1128/MCB.24.15.6871-6886.2004.

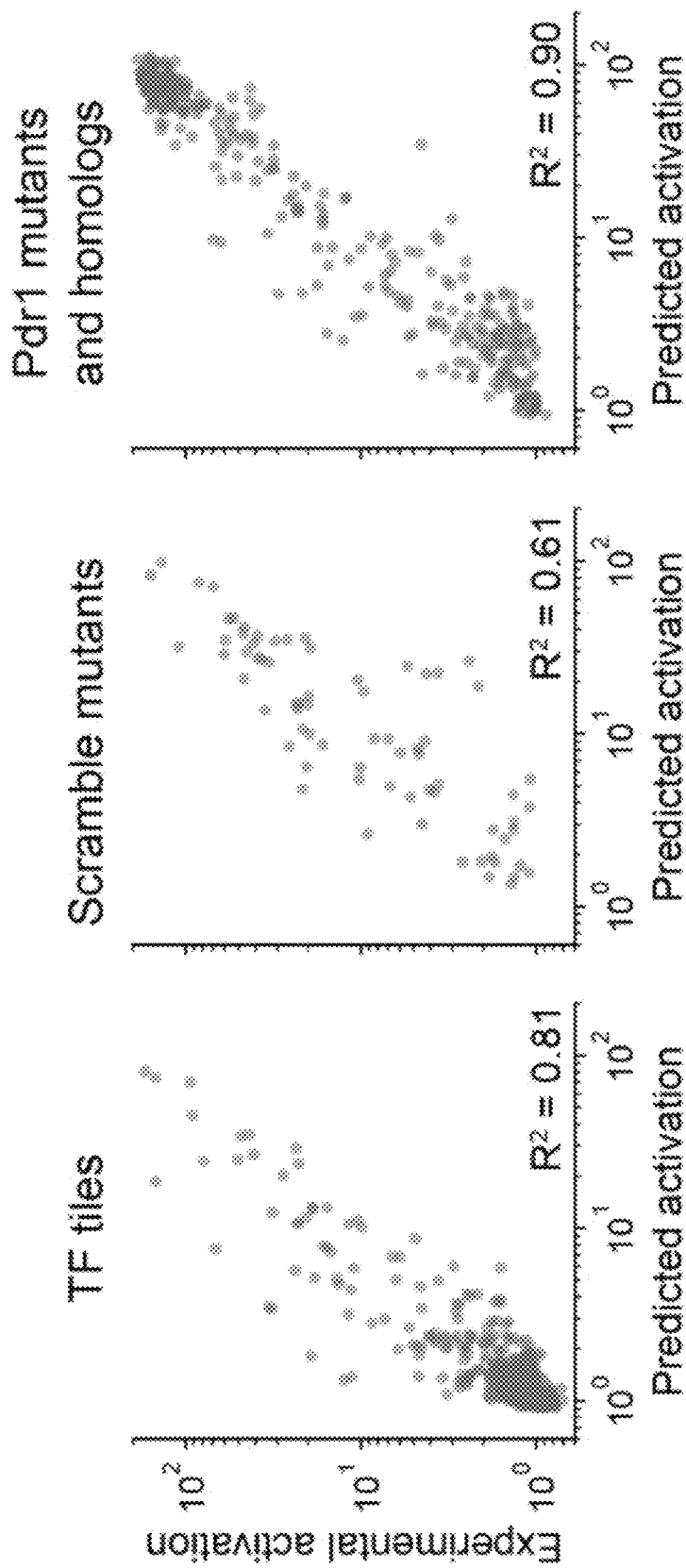
Figure 2B1  Figure 2B2  Figure 2B3

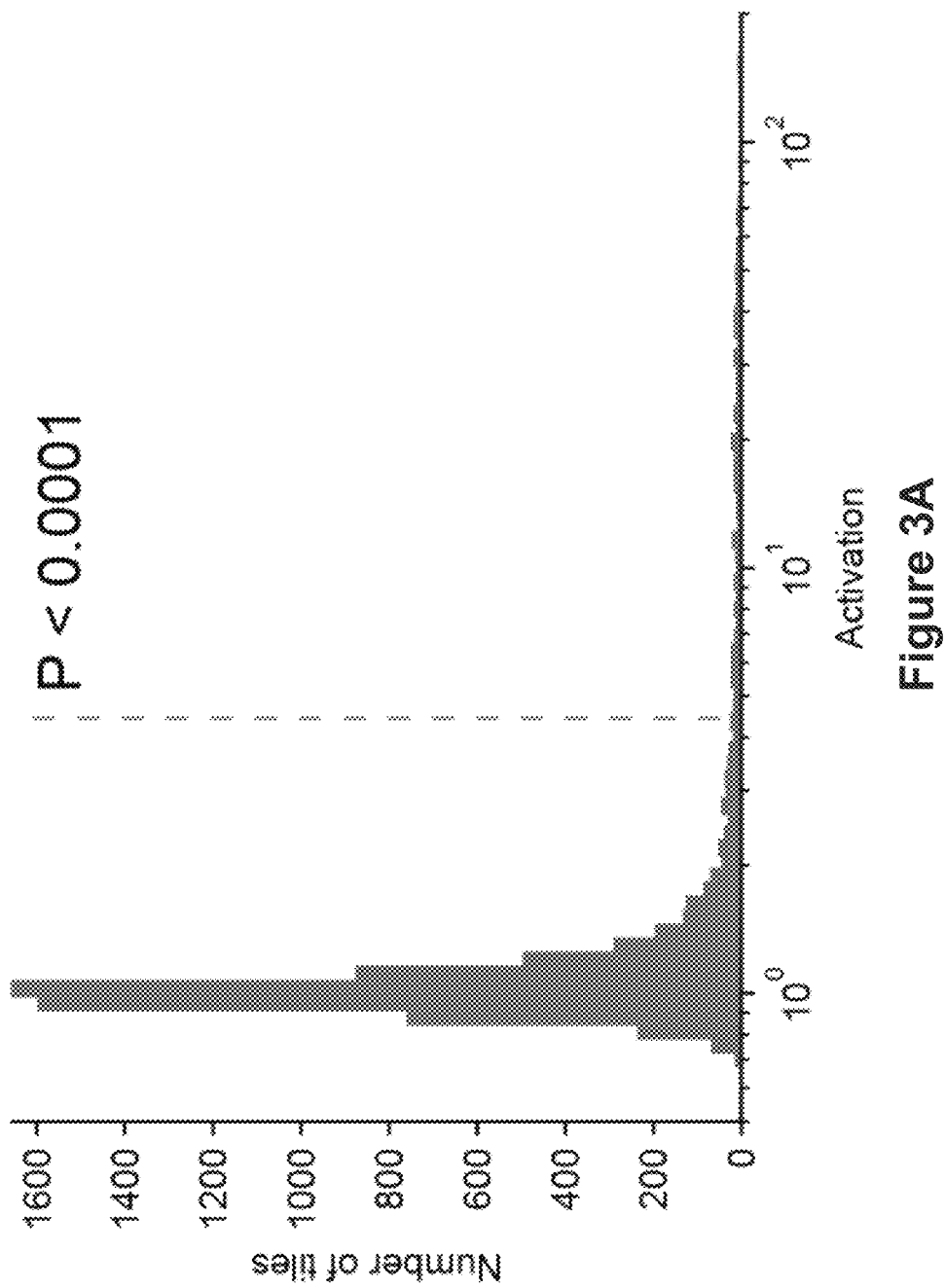

SYSTEMS AND METHODS TO IDENTIFY TRANSCRIPTION FACTOR ACTIVATION DOMAINS AND USES THEREOF

CROSS-REFERENCE TO RELATED APPLICATIONS

The current application claims priority to U.S. Provisional Patent Application No. 63/125,836, entitled "Systems and Methods to Identify Transcription Factor Activation Domains and Uses Thereof" by Roger D. Kornberg et al., filed Dec. 15, 2020; the disclosure of which is hereby incorporated by reference in its entirety.

STATEMENT REGARDING FEDERALLY SPONSORED RESEARCH OR DEVELOPMENT

This invention was made with Governmental support under Contract Nos. 133097 and 11696 awarded by the National Institutes of Health. The government has certain rights in the invention.

FIELD OF THE INVENTION

The present invention relates to transcription factors. More specifically, the present invention relates to systems and methods implementing machine learning models to identify activation domain regions of transcription factors.

BACKGROUND

Transcription factors (TFs) play a key role in eukaryotic cell pathways by modulating the expression of genes in response to a signal. They are thus involved in all central processes such as growth, stress response, and development, and when mis-regulated or mutated can lead to many human diseases. Each TF includes a family-determining DNA-binding domain (DBD) and an effector domain that regulates nearby gene transcription. Activation domains (ADs)—effector domains that increase transcription—have long been of particular interest due to their roles as oncogenic drivers and use as scientific tools.

ADs were discovered as regions which could independently stimulate transcription when ectopically recruited to a gene promoter. Early experiments showed that ADs were unlike structured domains because progressive truncations showed graded, proportional reductions in activity. Subsequent studies showed that ADs were high in predicted disorder and had few similarities in their primary sequence. Instead, ADs were classified based on their enrichment of certain residues, whether acidic, glutamine, proline, or other residues.

Acidic ADs are the most common and best characterized. Acidic ADs retain activity when transferred between yeast and humans, pointing to a conserved eukaryotic mechanism. While some have found that acidic residues are necessary for activation, others have found that they are dispensable. Besides their negative charge, acidic ADs are abundant in bulky hydrophobic residues. Mutating these hydrophobic residues reduces activation, often In proportion to the number mutated.

Because AD sequences are highly diverse and poorly conserved, only a small fraction of all ADs have likely been annotated. Sequence motifs have been proposed based on analysis of select ADs but have not been used for large-scale prediction. Screens of random sequences identified numerous, heterogeneous activating sequences that represented as much as 1-5% of elements tested. However, wild-type protein sequences and structures are highly non-random, so predictions based on random sequence may not generalize. On the other hand, direct screening of wild-type sequences has identified only modest numbers of ADs at coarse resolution. As of yet, there lack methods to experimentally detect or computationally predict the full diversity of wild-type ADs.

SUMMARY OF THE INVENTION

This summary is meant to provide some examples and is not intended to be limiting of the scope of the invention in any way. For example, any feature included in an example of this summary is not required by the claims, unless the claims explicitly recite the features. Various features and steps as described elsewhere in this disclosure may be included in the examples summarized here, and the features and steps described here and elsewhere can be combined in a variety of ways.

In one embodiment, a method includes obtaining a convolutional neural network (CNN), where the CNN is trained with functional activation domain data from a first organism and identifying an activation domain in a second organism using the CNN.

In a further embodiment, the functional activation domains are described by at least one of: peptide sequence, predicted secondary structure, actual secondary structure, predicted disorder, and activity of the functional activation domain.

In another embodiment, the method further includes obtaining the functional activation domain data and training the CNN with the functional activation domain data.

In a still further embodiment, obtaining functional activation domain data includes obtaining a library of nucleic acid molecules, where each molecule in the library of nucleic acid molecules encodes a peptide including a DNA-binding domain and a potential activation domain, providing the library to a collection of cells, where each cell in the collection of cells includes a target gene operatively coupled to a promoter region to which the DNA-binding region binds, screening the collection of cells for a cell that expresses the target gene, which indicates a functional activation domain within the molecule from nucleic acid molecules provided to the cell, and identifying the functional activation domain in the library.

In still another embodiment, identifying the functional domain includes sequencing the nucleic acid molecule introduced into the cell.

In a yet further embodiment, the method further includes screening the collection of cells for a cell that expresses the molecule from the library of nucleic acid molecules.

In yet another embodiment, the peptide further includes a reporter domain.

In a further embodiment again, the reporter domain is selected from mCherry, GFP, YFP, RFP, DsRed, mStrawberry, mOrange, and dTomato.

In another embodiment again, screening the collection of cells for a cell that expresses the target gene simultaneously screens the collection of cells for a cell that expresses the molecule from the library of nucleic acid molecules.

In a further additional embodiment, identifying the functional activation domain includes sequencing the molecule from the library of nucleic acid molecules introduced to the cell.

In another additional embodiment, the peptide further includes an inducer domain, and the method further includes inducing expression of the target gene.

In a still yet further embodiment, inducing expression includes providing an exogenous chemical to the collection of cells.

In still yet another embodiment, the inducer is an estrogen inducer, and the exogenous chemical is estrogen.

In a still further embodiment again, the collection of cells are selected from bacteria, yeast cells, plant cells, and mammalian cells.

In still another embodiment again, the collection of cells are yeast cells.

In a still further additional embodiment, the CNN possesses 1-20 hidden layers.

In still another additional embodiment, the CNN possesses 3-9 convolutional layers.

In a yet further embodiment again, the CNN possesses 9 convolutional layers of kernel size 10 and channel width 30.

In yet another embodiment again, the first organism and the second organism are different species.

In a yet further additional embodiment, the method further includes obtaining the functional activation domain data and training the CNN with the functional activation domain data, where the CNN possess 1-20 hidden layers and 3-9 convolutional layers, where the convolutional layers possess kernel size 10 and channel width 30 and the functional activation domains are described by at least one of: peptide sequence, predicted secondary structure, actual secondary structure, predicted disorder, and activity of the functional activation domain.

Other features and advantages of the present invention will become apparent from the following detailed description, taken in conjunction with the accompanying drawings which illustrate, by way of example, the principles of the invention.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

FIGS. 2A-2F illustrate exemplary data showing the efficacy to identify activation domains in accordance with various embodiments of the invention.

FIGS. 3A-3D illustrate exemplary data of identifying activation domains in accordance with various embodiments of the invention.

DETAILED DESCRIPTION

Figure 1A:
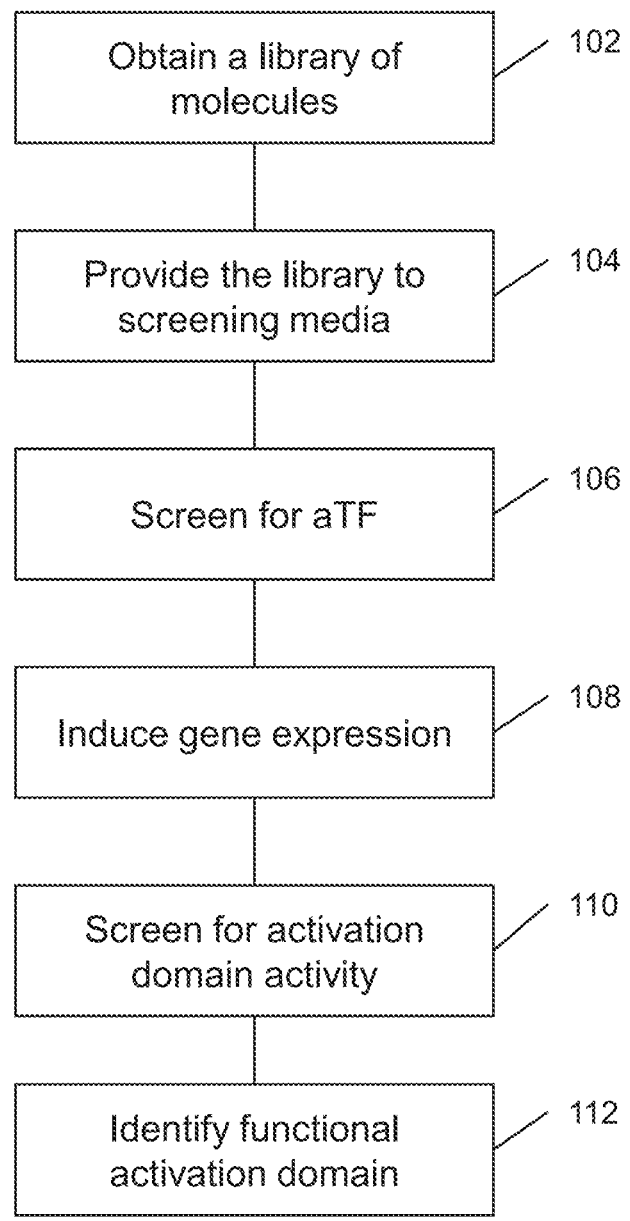
FIGS. 1A-1E illustrate methods and exemplary data of identifying activation domains in accordance with various embodiments of the invention.

Turning now to the drawings, systems and methods to identify transcription factor activation domains and uses thereof are provided. Many embodiments utilize machine learning methodologies to identify peptide sequences, domains, motifs, or regions capable of activating gene transcription. Additional embodiments design and/or construct peptides to activate gene transcription in vivo and/or in vitro. Certain embodiments design nucleic acid sequences (e.g., DNA and/or RNA) that encode such custom peptides. Further embodiments treat an organism, such as a human, with one or more of a nucleic acid sequence and a peptide encoding for a custom transcription factor, such that it activates or increase expression of one or more genes within the organism.

Transcription factor proteins play a key role in cell pathways by modulating the expression of genes in response to a signal. They are thus involved in all central processes such as growth, stress response, and development, and when mis-regulated or mutated can lead to many human diseases. Transcription factors are also used by viruses to hijack and direct a host cell's processes towards amplifying the virus. Furthermore, transcription factors are used extensively as research tools and in engineering cellular circuits.

Activation domains are the regions of transcription factors that are responsible for increasing expression of a gene. However, very few activation domains in human or virus genomes are annotated, because they are poorly conserved in sequence even though they are highly conserved in function. Many embodiments describe a computational tool to predict locations and strengths of activation domains from protein sequence to enable rapid functional characterization of transcription factors across all newly sequenced genomes and of genetic mutants, whether due to natural genetic variation in humans or viruses or arising in diseases such as cancer. Such embodiments also enable rational design of activation domains with varying strengths for use as research tools and for cellular engineering.

Many embodiments herein utilize a dataset of in vivo activation and/or in vitro coactivator-binding domains to train a machine learning model, such as a convolutional neural network, to identify activation domains and strengths of these domains in organisms (e.g., eukaryotes) and/or tissues (e.g., cancers). In certain embodiments, the in vivo activation and/or in vitro coactivator-binding domains arise from experimental work identifying activation domains in one or more species, such as a model species (e.g., yeast, *Arabidopsis* spp., mouse, rat, etc.).

Many embodiments are capable of identifying core regions of all ADs responsible for activation and dissect the sequence and mechanistic determinants of coactivator elements (e.g., Mediator).

It should be noted that within the context of this description the term "in vivo" refers to "in an organism" and/or "in a cell line" (e.g., tissue culture), and the term "in vitro" refers to "in a solution" and/or "in a test tube."

Identifying Activation Domains

Turning to FIG. 1A, many embodiments are directed to a method 100 to identify activation domains. Many of such embodiments obtain activation measurements from amino acid segments representing a portion of a longer protein or peptide. In many embodiments, these activation measurements are quantitative, uniform, and high-throughput.

At 102, many embodiments obtain a library of molecules. Various embodiments obtain a library of proteins or peptides comprising one or more functional domains, and certain embodiments obtain a library of nucleic acid molecules (e.g., RNA and/or DNA) that encode for a peptide with one or more functional domains. In many embodiments, each molecule in the library comprises a DNA binding domain and a potential activation domain. Additional embodiments include additional elements for identification and/or induction of gene activation—for example, some embodiments include a reporter peptide (e.g., mCherry, GFP, YFP, RFP, DsRed, mStrawberry, mOrange, dTomato, and/or any other known reporter molecule), and additional embodiments include an inducer, such as an estrogen response domain and/or any other domain that can localize the molecule to the nucleus and/or induce gene activation via an exogenous treatment.

Figure 1B:
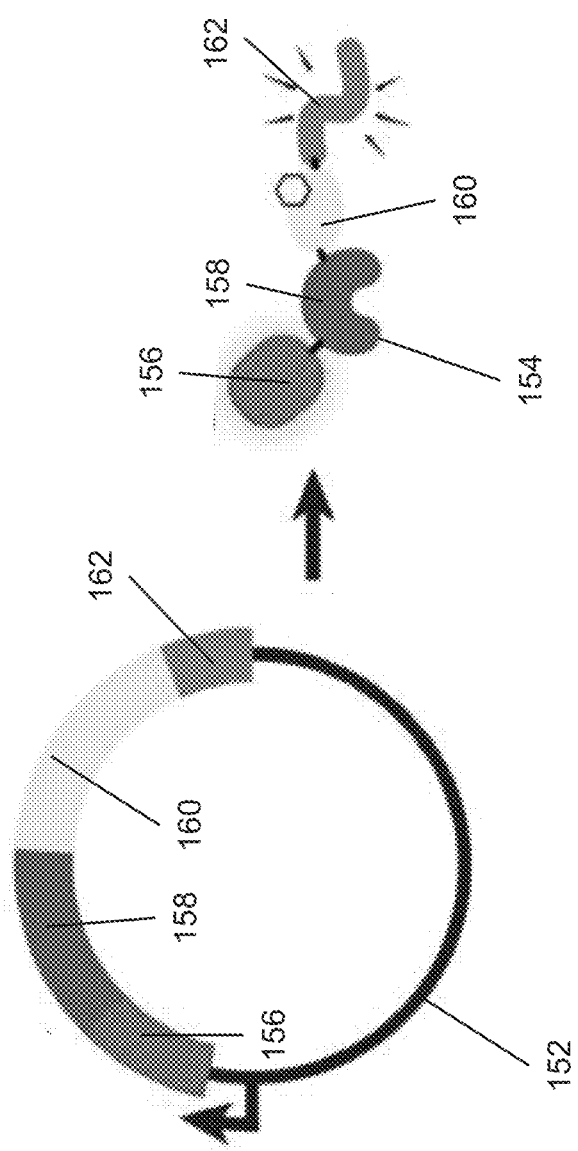

FIG. 1B illustrates an exemplary nucleic acid molecule 152 and exemplary amino acid molecule 154 (also known as an artificial transcription factor or aTF), which can be encoded by the nucleic acid molecule 152. As illustrated in FIG. 1B, nucleic acid molecule 152 possesses an open reading frame encoding for a reporter domain 156, a DNA-binding domain 158, an inducer domain 160, and a potential activation domain 162. When translated to an aTF 154, reporter domain 156 can identify localization of the molecule via florescence (e.g., using mCherry or another fluorescent moiety) or any other method for identifying localization of specific proteins and quantify the total expression level of the aTF inside each individual cell. Additionally, DNA-binding domain 158 can identify a specific DNA sequence, such as a promoter region of a target gene. In some embodiments, the target gene is a reporter gene (e.g., a fluorescent marker, such as those listed elsewhere herein). Inducer domain 160 allows for induction of the gene expression by effecting movement of the aTF 154 to a nucleus or by encouraging DNA binding of the aTF 154 to the specific sequence to which DNA-binding domain 158 binds. In certain embodiments, an estrogen response domain is used as the inducer domain 160, such that introduction of exogenous estrogen induces expression of a target gene. Finally, the potential activation domain 162 has the potential to directly or indirectly recruit an RNA polymerase to transcribe a gene—e.g., if the potential activation domain 162 actually has activation activity, a target gene will be transcribed via a recruited polymerase, while potential activation domain 162 without activation activity will not recruit a polymerase to transcribe a target gene.

Figure 1C:
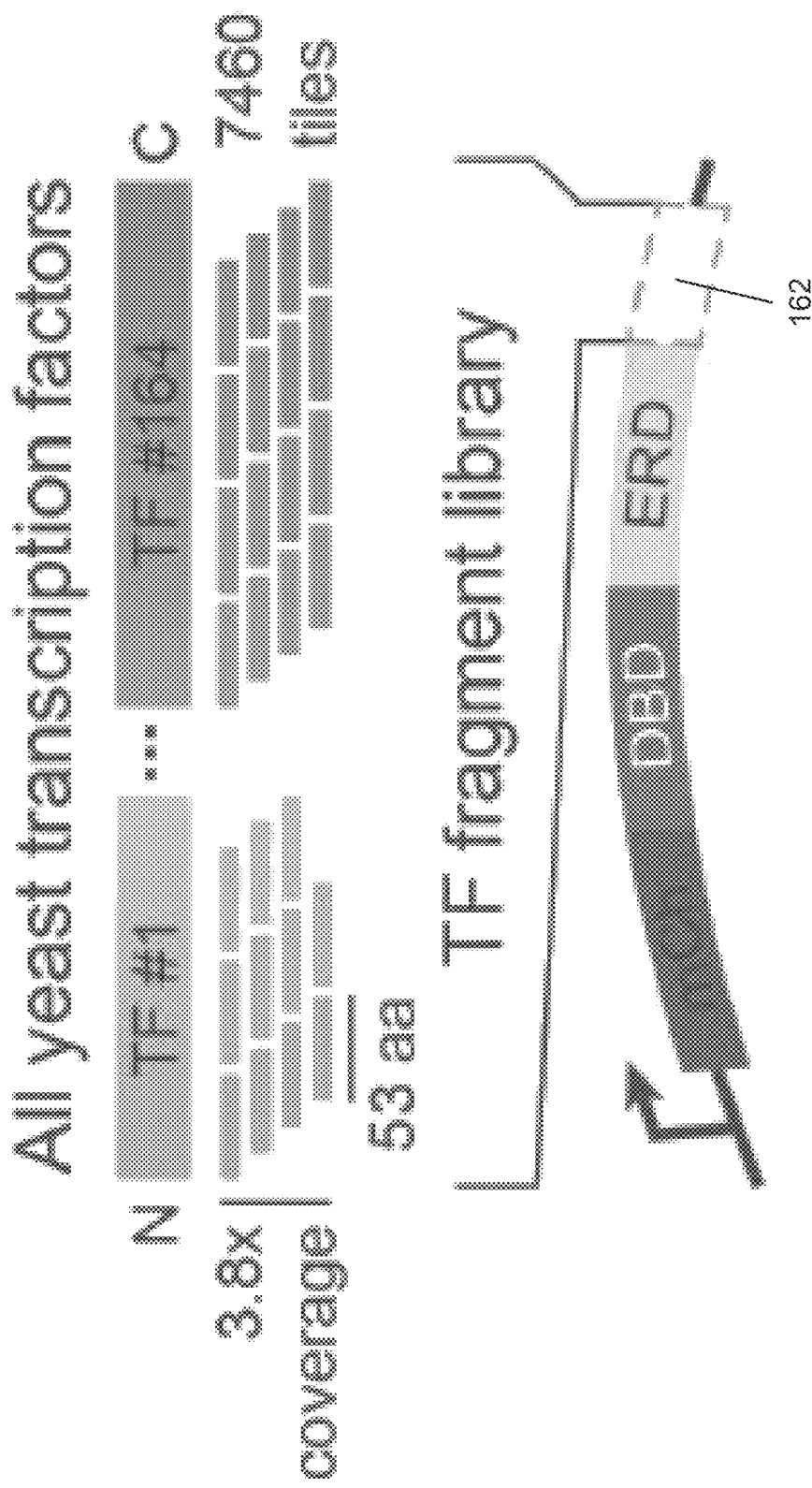

In many embodiments the potential activation domain is a segment of a known transcription factor protein. Additional embodiments possess segments of other known proteins, and further embodiments possess random amino acid segments. In some embodiments using segments of known proteins, the potential activation domain represents a tile from a sliding window of a protein's amino acid sequence—e.g., amino acids 1-25, amino acids 2-26, amino acids 3-27, etc. FIG. 1C illustrates a non-limiting example of a tiling strategy implemented for all yeast transcription factors. As illustrated in FIG. 1C, 7,460 segments, each 53 amino acids (aa) in length, tiled all 164 yeast transcription factors with 3.8-fold coverage. Each segment was cloned into a unique aTF expression plasmid as a potential activation domain 162.

In certain embodiments, the potential activation domain is a segment of a constant amino acid length (e.g., each molecule possesses a potential activation domain with the same segment length, such as 53 amino acids). In some embodiments, the potential activation domain is a segment of a variable amino acid length (e.g., molecules within the library possess a potential activation domain of varying sizes, such as segments ranging between 15-60 amino acids).

As noted above, certain embodiments obtain a library of nucleic acid molecules that encode for a protein or peptide, such as described. As such, each nucleic acid molecule encodes one or more of a DNA binding domain and a potential activation domain, a reporter peptide, an inducer, such as described herein. Additional embodiments of nucleic acid molecules further encode for one or more functional regions on the molecule, such as a promoter, a terminator, an origin of replication, a splice site, a start codon, a stop codon, a poly-A tail, and/or any other nucleic acid sequence that can aid in replication or expression of the molecule. In some such embodiments, the molecules in the nucleic acid library are circular (e.g. plasmids, BACs, etc.), while in some embodiments, the nucleic acid is linear.

Figure 1D:
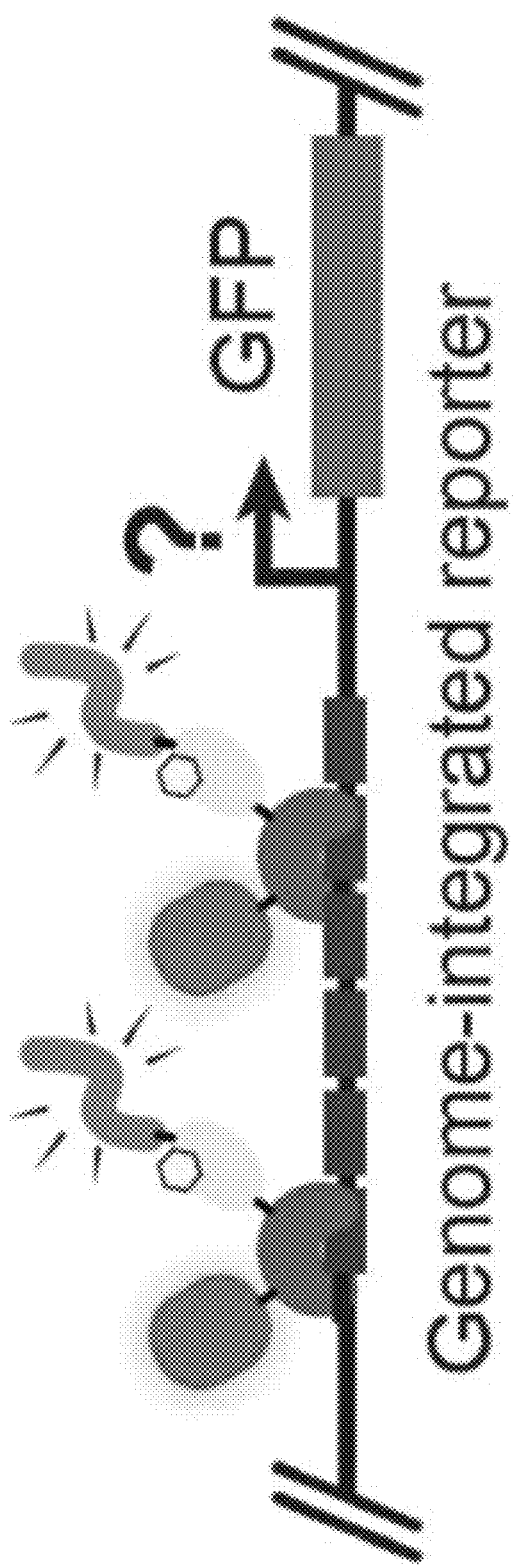

Turning to FIG. 1D, an example of an aTF 154 in action, in accordance with many embodiments is illustrated. In numerous embodiments, one or more aTFs 154 interact with a piece of segment of DNA 180, such as a gene promoter, via the aTF's DNA-binding domain 158. Such interaction can be induced via an induction system, as described elsewhere herein. In many embodiments, if the potential activation domain 162 is effective in activating gene expression, a target gene 182 is transcribed. As described elsewhere, the target gene 182 can be a reporter gene, such as those recited elsewhere herein.

Returning to FIG. 1A, at 104, various embodiments provide the library of molecules into a screening media. In some embodiments, the screening media is an in vivo media, such that the library of molecules are inserted into cells. In some in vivo methods, the library of molecules is introduced to cells at a concentration that no cell should receive more than one molecule from the library of molecules. In certain embodiments, the cells are selected from bacteria (e.g., *Escherichia coil*), plant cells (e.g., *Nicotiana benthamiana*), yeast cells (e.g., *Saccharomyces cerevisiae*), mammalian cells (e.g., *Mus musculus*), and/or any other relevant type of organism or cell that can be cultured.

At 106, various embodiments screen for aTF presence. In embodiments using cells, the cells can be screened or sorted (e.g., via flow cytometry) to select for cells that include a molecule from the library of molecules, such as embodiments which encode a reporter moiety on the aTF (e.g., FIG. 1B, reporter domain 156). Additionally, some embodiments identify a quantitative level of aTF expression. In such embodiments, the expression level and/or presence of the aTF molecules can be qualitatively and/or quantitatively determined via the presence of a reporter domain.

At 108, some embodiments induce gene expression. Induction can include translocating an aTF to a nucleus or by encouraging DNA binding of a DNA-binding domain. Various gene induction systems are known in the art, such as an estrogen induction system, where introduction of exogenous estrogen leads to expression of a target gene. Some embodiments do not require induction via exogenous control, such that target gene expression proceeds regardless of exogenous control.

Further embodiments screen for activation domain activity at 110. Expression within a cell or aliquot is indicative of effective aTFs (e.g., aTFs possessing activation domains with activation activity). In many embodiments, the target gene is a reporter gene, such as a fluorescent molecule. As such, many embodiments screen cells via flow cytometry, a plate reader, and/or any other method to identify target gene expression. In various embodiments, expressing cells and/or aliquots are isolated from non-expressing cells and/or aliquots. Some embodiments provide a quantitative measurement of activation as a measurement of the target gene, such as through fluorescence (if the target gene is a fluorescent reporter gene) or other methodology to quantify expression, such as qPCR.

At 112, many embodiments identify a functional activation domain from the expressing cells and/or aliquots. In many of these embodiments, the activation domains are sequenced via protein sequencing and/or nucleic acid sequencing. For example, in embodiments where the library of molecules are nucleic acids, the nucleic acid sequence can identify the underlying amino acid sequence based on codon usage.

Figure 1E:
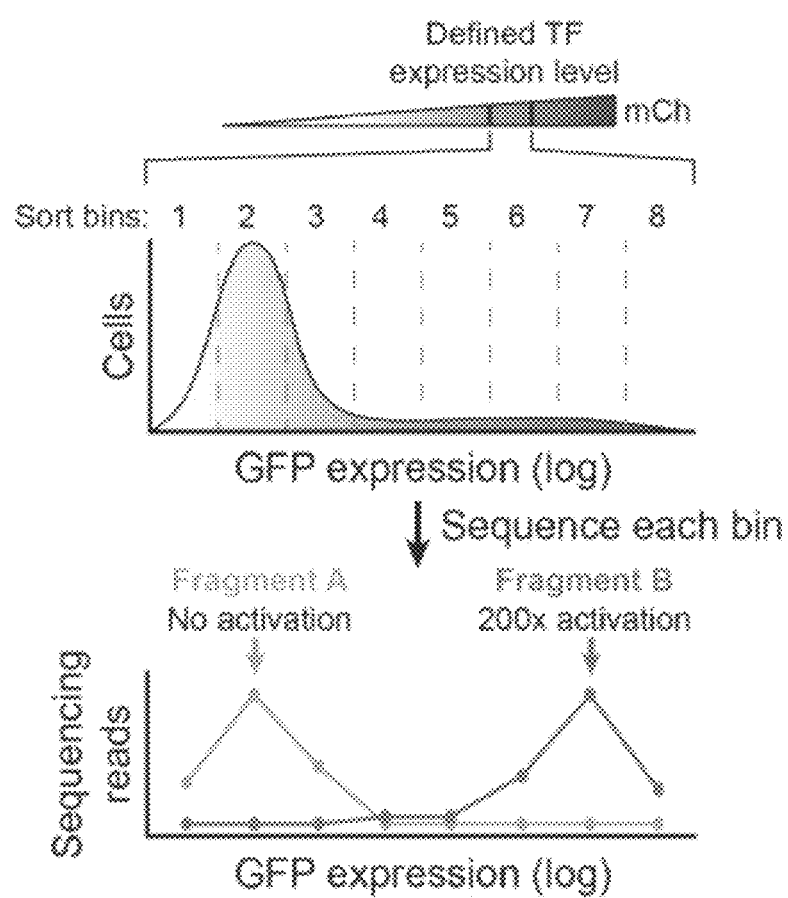

FIG. 1E illustrates exemplary data showing identification of potential activation domains or fragments by measuring expression via fluorescence (mCherry for the aTF and GFP as the target gene), which can be used to identify the activation domain sequence. In some embodiments, the target gene expression is normalized to aTF expression level to quantify activation domain activity that can be compared across aTFs, while some embodiments select a specific level of aTF expression for comparison. In the exemplary embodiment, target gene expression (e.g., GFP) are used as bins for activation activity of the aTF. Then, aTFs are sequenced to identify which specific activation domain sequence provides activation activity and how much activity it provides.

Various embodiments perform features of method 100 in different order, omit certain features, and/or repeat certain features. For example, if no induction is necessary, inducing gene expression 106 may be omitted, while screening steps, such as identifying expressing cells 108 can be repeated, such as to set an expression threshold and/or limit sequencing costs and/or sequencing resources. Additionally, some embodiments quantitatively screen for expression of an aTF and expression of the target gene at the same time through a methodology that can both quantify and identify multiple targets, such as multi-channel fluorescence, qPCR, nucleic acid sequencing, or any other suitable method to quantify expression.

Further embodiments repeat the entire process with a different size or sizes of potential activation domains to identify smallest possible unit with activation activity, while some embodiments (in addition to or instead of) repeat the entire process with one or more alterations in the amino acid sequence, either through an alteration in a nucleic acid sequence or alteration of an amino acid sequence, to identify a key residue or key residues that contribute to activation activity.

Deep Learning Models to Identify Activation Domains

As some genetic diseases can be resolved by regulating a gene (either up-regulating or down-regulating), identifying domains that activate gene transcription can give rise to therapeutics to control genes. As such, certain embodiments utilize a machine learning model, such as a neural network, to identify activation domains in proteins, organisms, and/or species. In many of these embodiments, a convolutional neural network (CNN) is trained based on known activation domains. In some of these embodiments, the identities of activation domains are obtained by methods described herein. Some embodiments further include quantitative measurements of activation activity for the activation domains. Some of these embodiments train the neural network on the amino acid composition of the known activation domains, and certain embodiments further train the neural network based on one or more of the following predicted secondary structure, actual secondary structure, and predicted disorder of the activation domain (see e.g., Oates, M. E., et al. (2012). D2P2: database of disordered protein predictions. Nucleic Acids Research 41, D508-D516; the disclosure of which is hereby incorporated by reference herein in its entirety.)

Figure 2A:
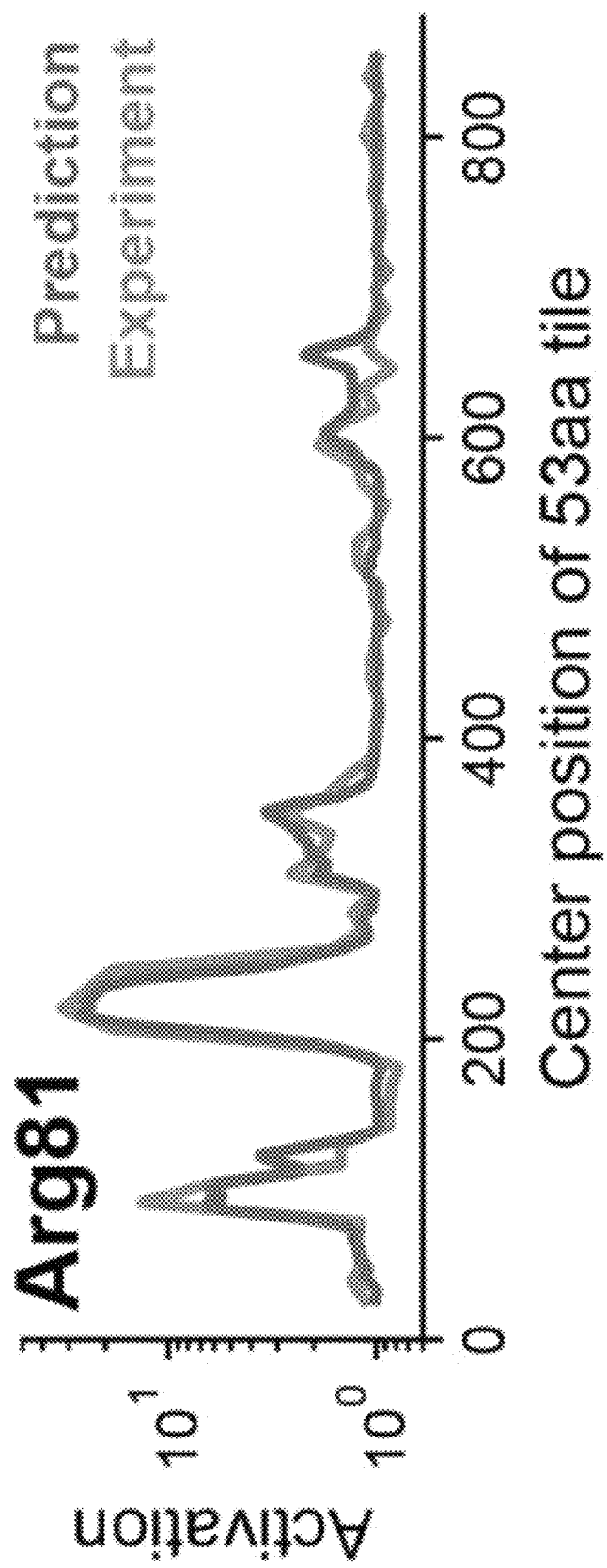

CNNs in accordance with many embodiments evaluate sequences by hierarchically integrating matches to a diverse suite of learned motifs. Such CNNs and have recently found great success in many genomic prediction tasks. Based on such methodologies, many embodiments explain greater than 80% of observed variation in data withheld from training, markedly better than an amino acid composition-based predictor. Many embodiments accurately predicted the activation strength of (1) new ADs within TFs omitted from training (FIG. 2A, FIG. 2B1); (2) scrambled AD sequences, despite their identical amino acid composition (FIG. 2B2); and (3) 232 mutants and 178 orthologs of the Pdr1 (FIG. 2B3). Altogether, many embodiments have validated performance across a diversity of both wild-type and mutant sequences.

Figure 2C:
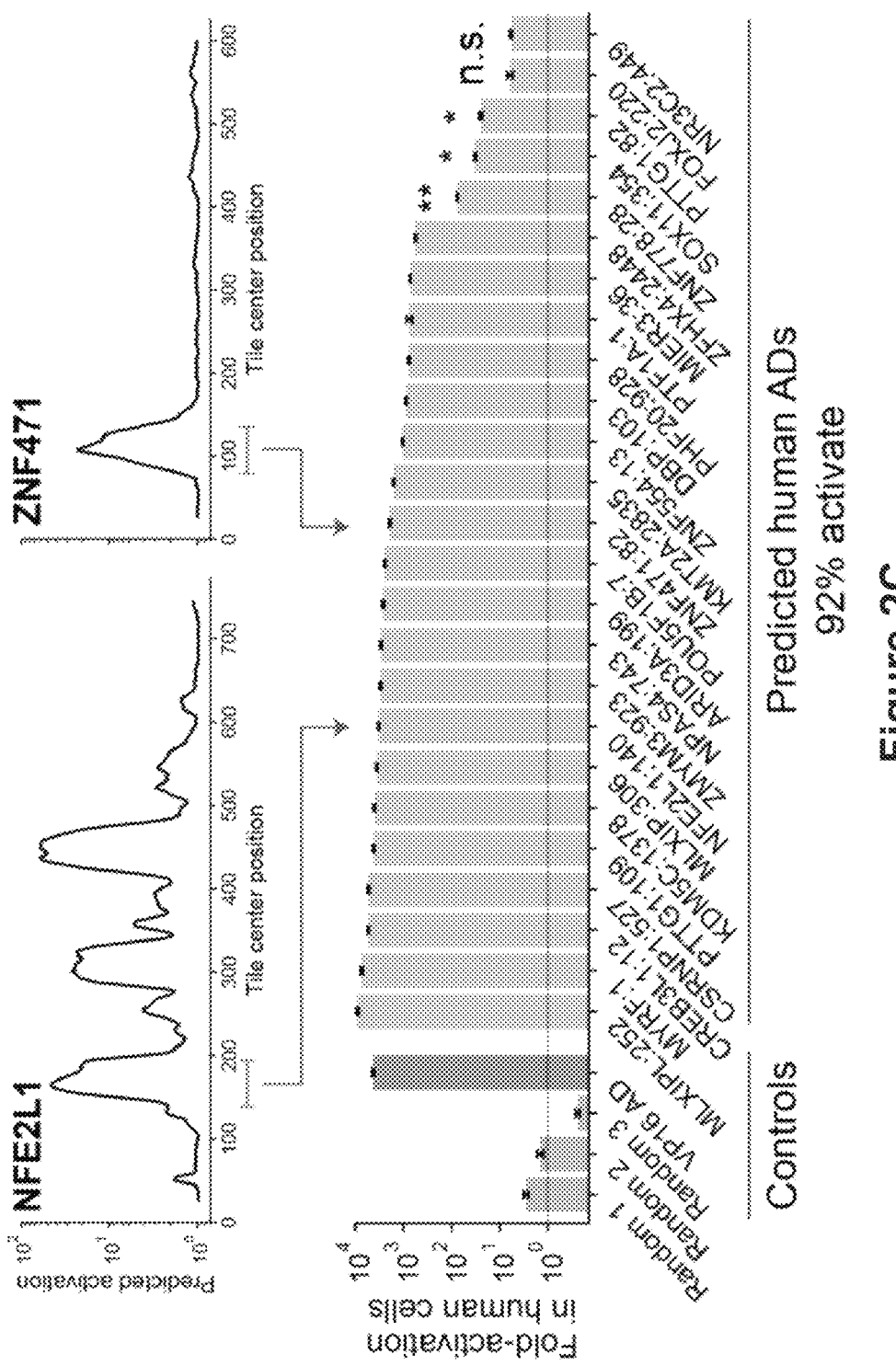
Figure 3B:
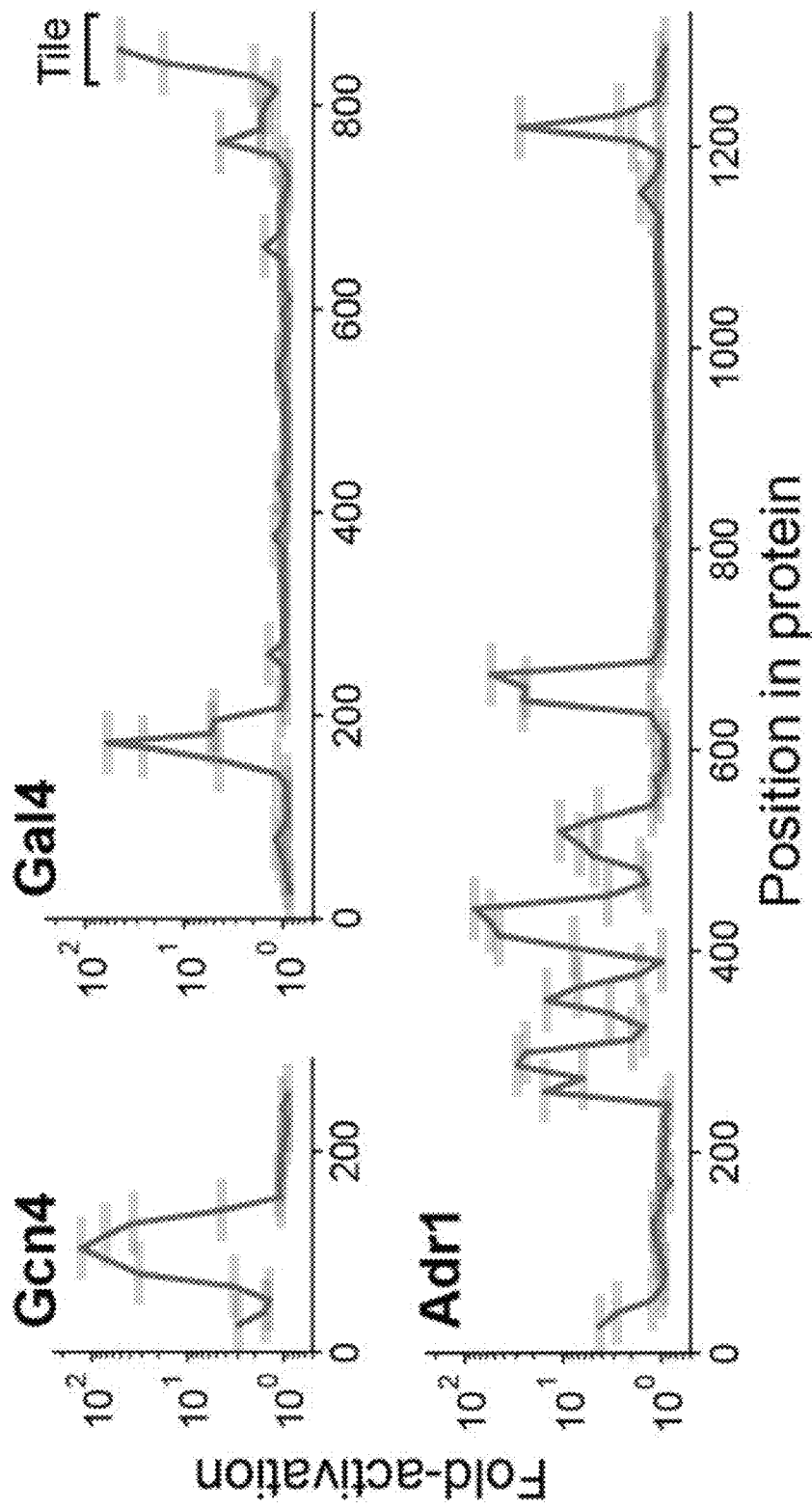
Figure 3C:
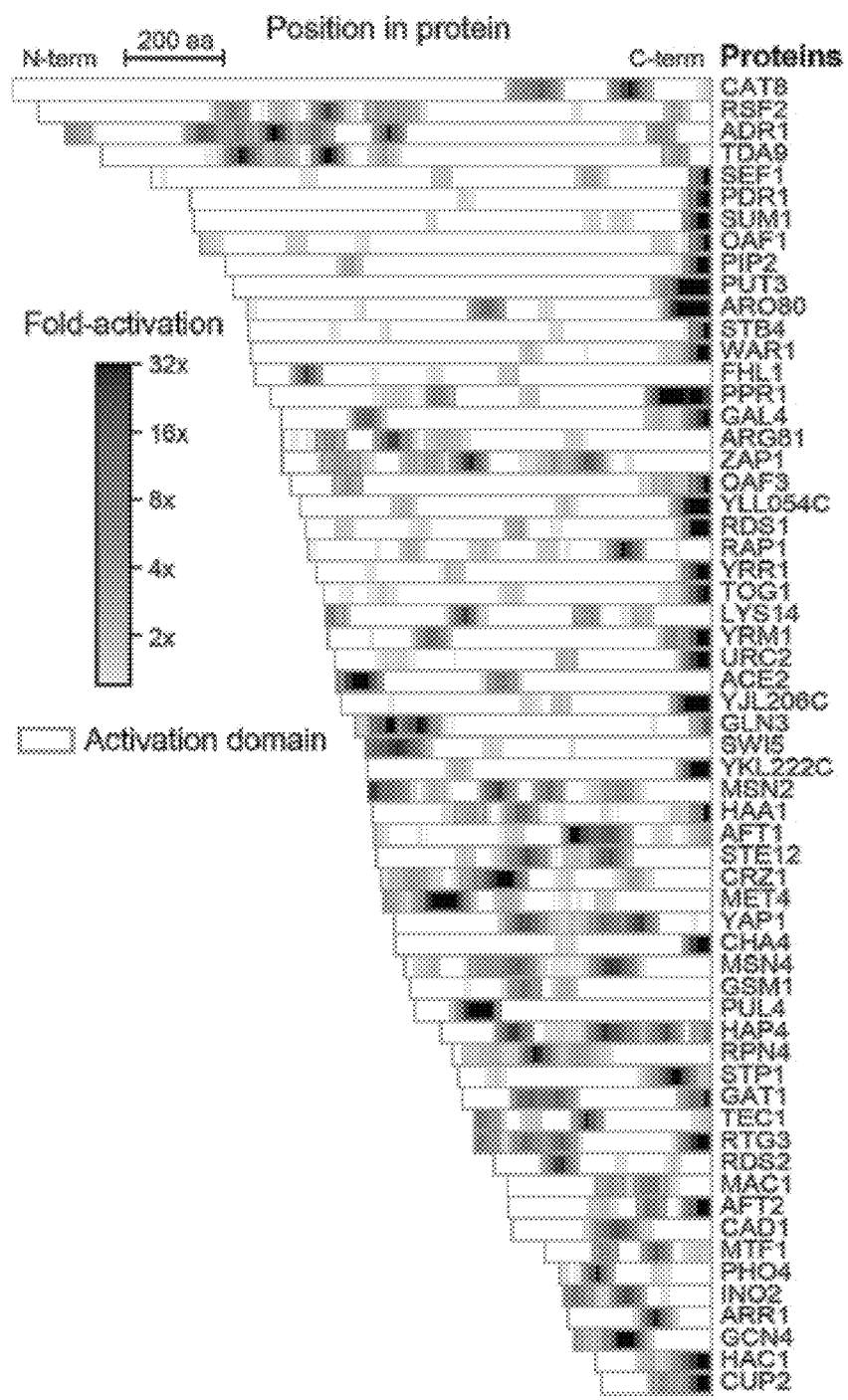
Figure 3D:
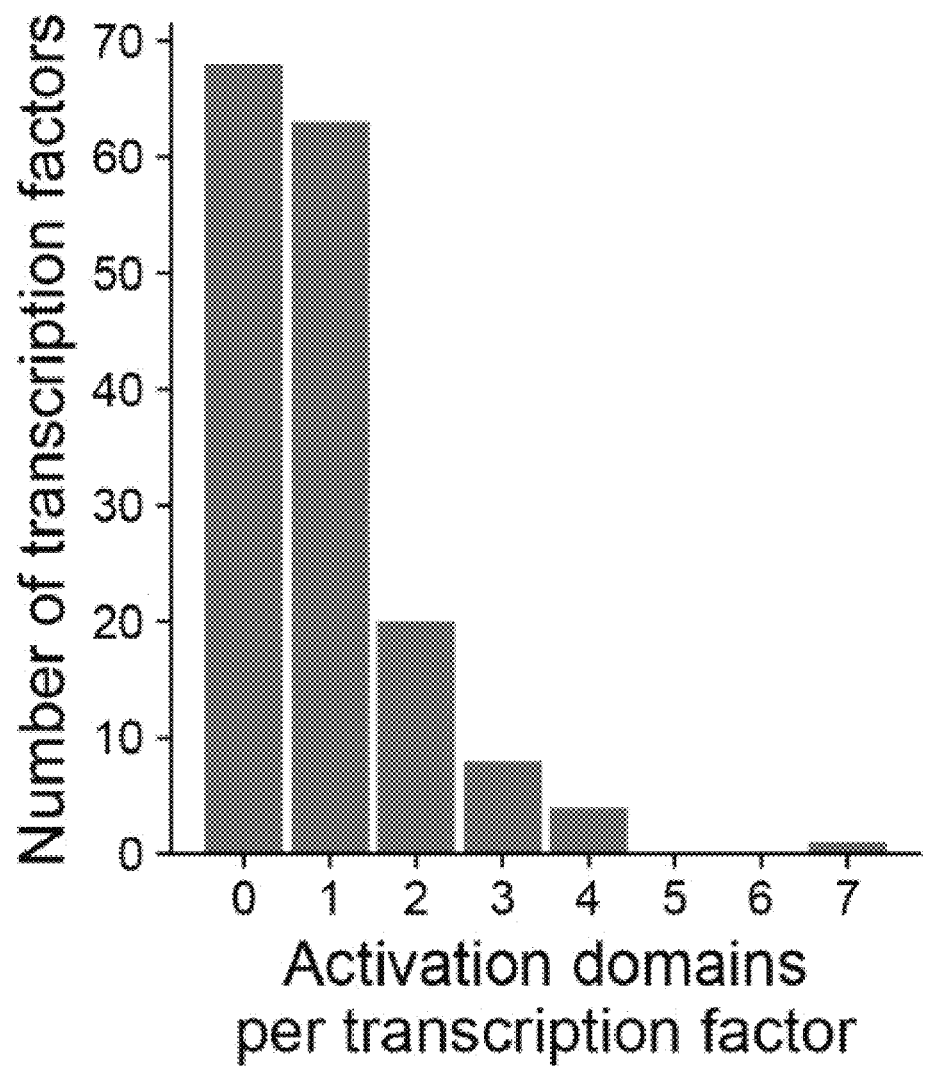

Turning to FIG. 2C, exemplary data showing the ability of embodiments to identify activation domains across species is illustrated. Specifically, FIG. 2C illustrates the capability to identify human activation domains using a CNN trained with yeast activation domain data. This exemplary embodiment predicted 271 high-strength and 366 moderate-strength ADs, together comprising 462 (27%) human TFs. These overlapped many known ADs of TFs from diverse families, including p53, NFkB, Myc, Klf4, E2F1, Fos, PPARA, SREBF1, and the glucocorticoid receptor. When tested experimentally, 25 high-strength human ADs were tested by activating a luciferase reporter in HEK293T cells. Twenty-three domains (92%) activated, including 6 domains that activated stronger than the prototypical VP16 AD (FIG. 2C). Another exemplary embodiment predicted 41 high-strength and 45 moderate-strength ADs in transcription-regulating viral proteins. Additional embodiments identify activation domains from organisms within the same species as the training data. For example, some embodiments identify activation domains in wild-type proteins and designed sequences. Further embodiments identify an effect of mutations on activation domains from organisms of the same species.

Figure 2D:
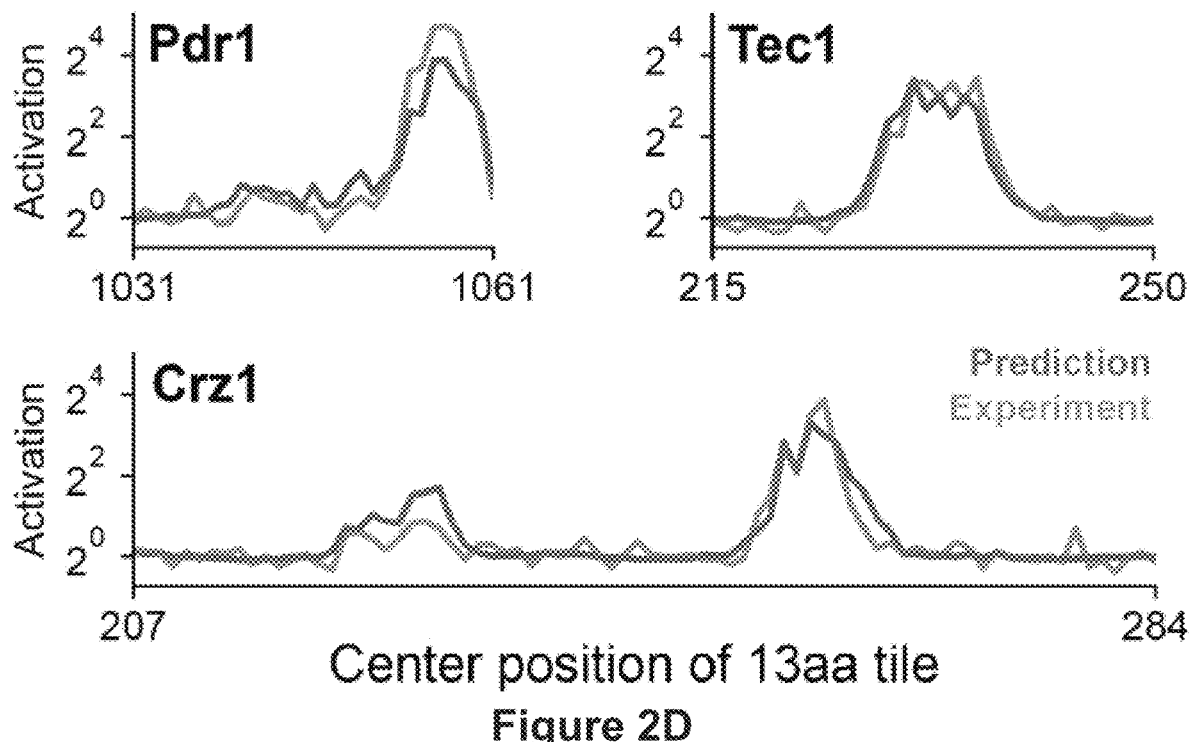

Turning to FIG. 2D, exemplary data showing that embodiments are capable of determining which amino acid segments activate. The exemplary embodiment in FIG. 2D identified short (<30aa) sequences suggesting that yeast ADs contain compact, independently activating regions. In this embodiment, these fragments were measured in vivo of 13aa-long fragments tiling 10 ADs in 1aa steps. This process identified "core" ADs within each of the ADs (FIG. 2D).

Figure 2E:
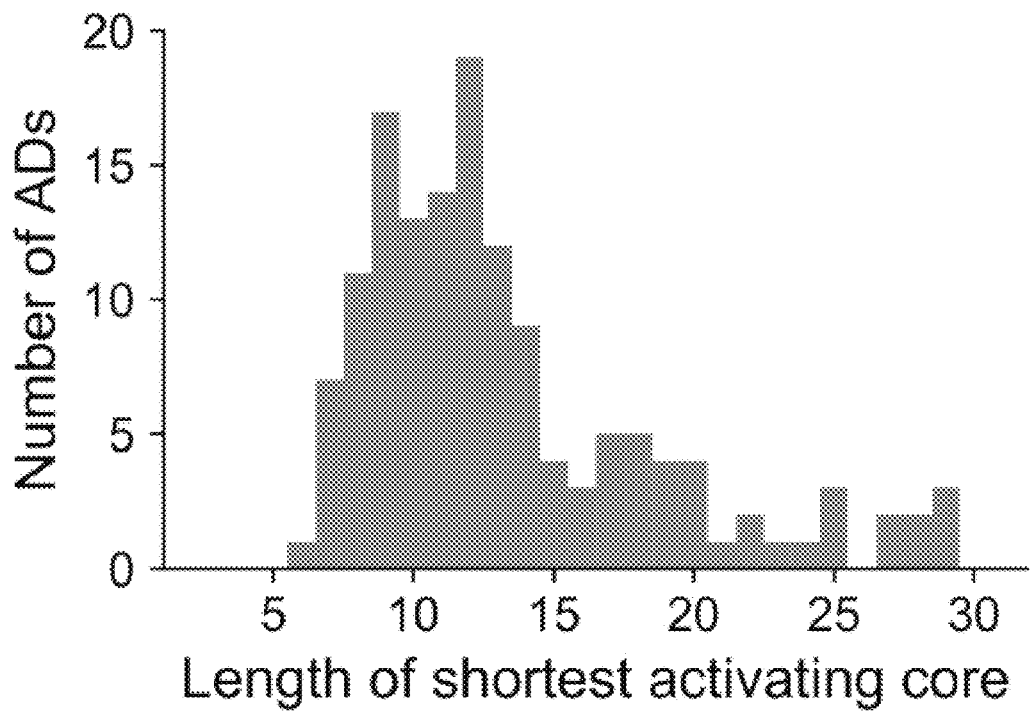
Figure 2F:
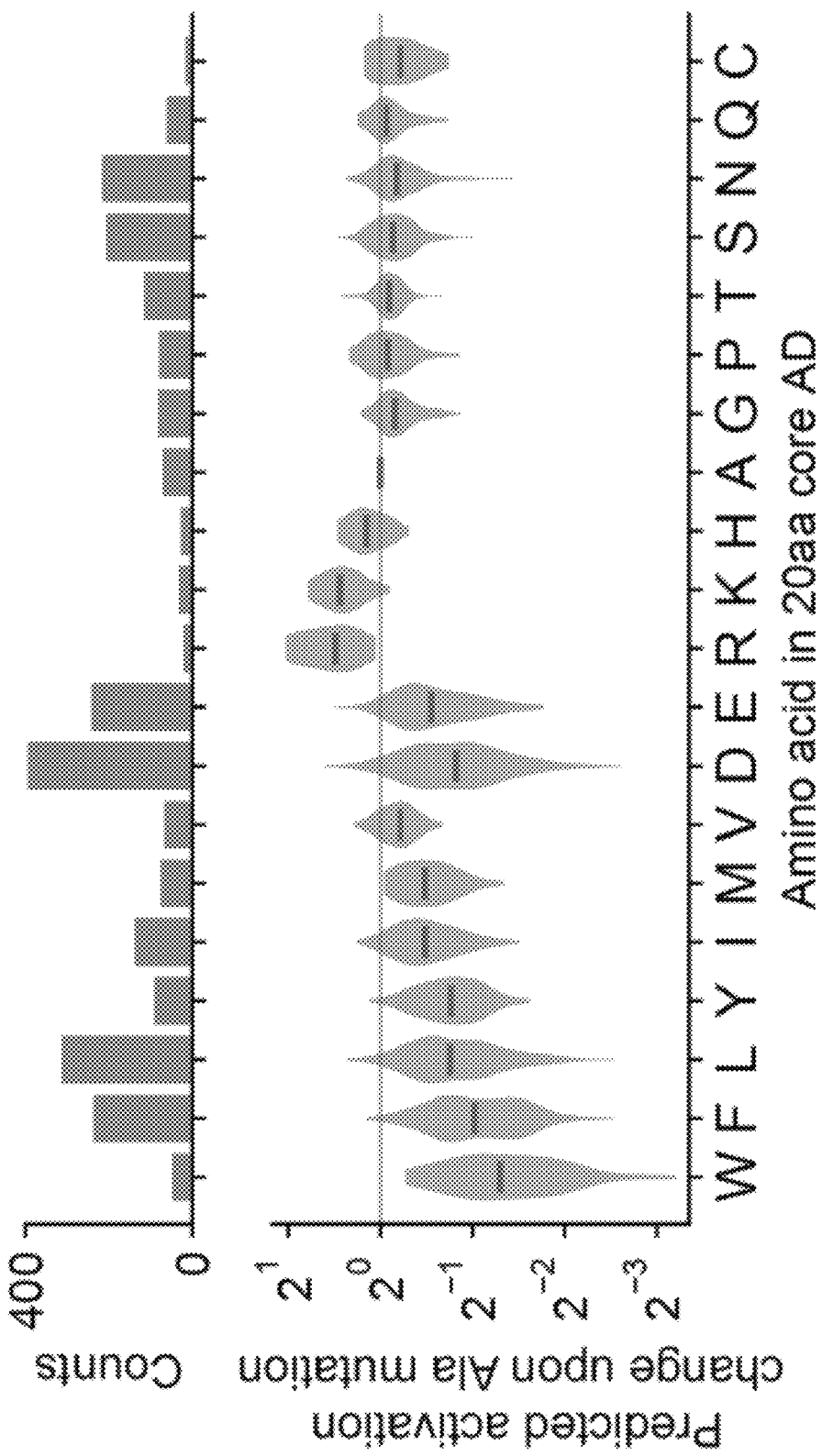

Some embodiments are able to identify the minimal region for activation. FIG. 2E illustrates exemplary data showing that embodiments are capable of identifying the minimal region within a 20aa core AD in 85% of all activation domains. Based on sequences identified within core activation domains, further embodiments can predict activation strength of mutations of specific amino acid residues. An exemplary embodiment showing alanine substituted for each residue is illustrated in FIG. 2F.

Implementations of Machine Learning Methodologies

Many embodiments utilize machine learning embodiments into processes to engineer organisms, including cells cultures, for research or industrial production. Such embodiments identify and characterize ADs in one or more systems of interest or design novel activation domains with specific activities for a particular use.

Further embodiments implement machine learning methodologies for genetic counseling by identifying impacts of naturally occurring or disease-related mutations, where the mutations affect the activation domain activity. As such, these embodiments could identify a disease or disease risk based on functional impact of a mutation.

Additional embodiments implement machine learning methodologies, such as those described herein, to determine clinical outcomes of mutations in cancers. Genetic fusions with activation domains are driving events in many cancers; however, cancers genome sequences are very different between patients so interpreting the functional effect of mutations in sequenced tumor genomes could be done using these embodiments.

Further embodiments implement such machine learning methodologies to determine clinical outcomes of mutations in viruses. Sequences of activation domains evolve quite quickly and can affect their activity in subtle ways. Thus, some embodiments predict how specific mutations in virus activation domains affects its function in the host cell.

Exemplary Embodiments

Experiments were conducted to demonstrate the capabilities of the assays and inhibitors in accordance with embodiments. These results and discussion are not meant to be limiting, but merely to provide examples of operative devices and their features.

Library Design

A peptide library was designed based on all 162 yeast (*Saccharomyces cerevisiae* S288C) transcription factors annotated with the Gene Ontology term GO:003700 (DNA-binding transcription factor activity), plus MET4 and HAP4, two yeast proteins known to be involved in transcription. Each transcription factor protein sequence was fragmented into 53-amino acid tiles with at least 40 amino acid overlap (overlap was adjusted based on the protein length to make the tiling as evenly distributed as possible across any given protein), yielding 7,457 unique peptides (sublibrary 1A-yeast-tiles). A set of 50 random synthetic (i.e., not derived from a known protein) sequences with the same amino acid frequencies as the overall set of yeast transcription factors (sublibrary 1A-random-control), as well as a set of 50 peptides derived from non-nuclear proteins (proteins not annotated with the GO term GO:0005634 (nucleus)) were used as controls (sublibrary 1A-yeast-nonnuclear). Note that there are no true negative controls; the random and non-nuclear sequences serve as references for comparison purposes, but it is unknown a priori whether they are strong or weak binders. Additionally, 10 positive control sequences previously reported to activate and bind Med15 were included (sublibrary 1A-yeast-controls). This gave a total of 7,567 unique 53-amino acid sequences.

Pairwise edit distance analysis demonstrates the diversity of peptide sequences in the library.

Across this library, 451 tiles showed significant activation ($P<0.0001$, FIG. 3A). When plotted by protein position, activating tiles clustered into discrete, well-defined ADs (FIG. 3B). Using a positional activation score, this embodiment systematically identified 150 ADs across 96 TFs (FIG. 3C). While 60 TFs contained just a single AD, 36 TFs had multiple, including up to seven distinct ADs in Adr1 (FIGS. 3B & 3D). C-terminal ADs were common—found in over half of all AD-containing TFs—and were stronger and shorter on average.

These 150 ADs included many (e.g., approximately 75%) of previously-reported ADs, showing this measurement was highly sensitive. A large amount (112) of the ADs were previously unknown. Furthermore, the 53aa tile length was not limiting, since ADs were identified in over 85% of full-length TFs that activated in a one-hybrid screen. In fact, AD-containing TFs upregulated a higher proportion of downstream genes than AD-less TFs, suggesting that these ADs are functional within the full-length protein. Together, these results show that this screen is both accurate and comprehensive and has yielded the first complete annotation of ADs in any eukaryotic genome.

Reverse Translation of Amino Acid Fragments to DNA Fragments

In the reverse translation design process, the aim was to optimize library DNA fragments for compatibility and consistency with an in vitro assay, standard RNA-seq protocols, and built-in redundancy for error-correcting reads. In particular, the Python package dnachisel 1.4.1 was used to optimize the following objectives:

- Use codons matching the relative frequencies in the rabbit species corresponding to the in vitro translation kit. Codon frequencies were pulled from the Codon Usage Database hosted by the Kazusa DNA Research Institute.
- Target an optimal GC content of 45% at both a local (sliding window of 50) level and a global (entire fragment) level.
- Avoid repeated subsequences of length 10 or more.
- Avoid homopolymer runs of 8 or more adenosines, 8 or more thymines, 5 or more cytidines, or 5 or more guanosines.
- Avoid adjacently repeated k-mers, specifically 3-peats of 3-mers or 5-peats of 2-mers.

An edit distance of 6 among the first 48 bases and last 48 bases of any two sequences in the same sublibrary was enforced. This was performed in a randomized, brute-force, iterative approach:

- At each iteration, pairwise edit distances were computed for all sequences in the sublibrary.
- If all pairwise edit distances are 6 or larger, the library is unchanged, and it was checked that none of the previously mentioned constraints are egregiously violated.
- For any sequence too similar to another sequence, 2 codons in the first 48 bases and 2 codons in the last 48 bases were randomly selected and changed while respecting the encoded amino acid sequence.
- Repeat.

Finally, it was verified that across each set of sequences sharing the same primer (e.g., all sequences in library 1A, or all sequences in library 1B), the total paired-end edit distance (sum of edit distance of 5'-most 50 bases and edit distance of 3'-most 50 bases) was at least 6.

Sequencing Read Alignment

The use of sequencing primers unique to each sublibrary enabled submission of samples for sequencing in multiplexed format and accurately assign reads to the correct sublibrary computationally. An edit distance margin built into the library was further leveraged to enable mapping of sequencing reads with a small number of errors.

Sequencing read alignment was performed using custom bash script built on top of existing tools and additional custom scripts. It takes as input arguments the UMI length, the sublibrary sequencing primer, the edit distance threshold for that sublibrary, and raw FASTQ files. Unique molecular identifiers (UMI) were extracted from reads and appended to the read names using umi_tools 1.0.0. cutadapt 1.18 was used to discard reads without matching paired-end sublibrary sequencing primers and trim the primers in reads with matching primers; the default error tolerance was used. bwa-mem 0.7.17-r1188 was used to perform a first-pass alignment of reads to the DNA fragment library. Imperfectly mapped read pairs (i.e., those without paired read SAM flags of 99 and 147) were re-mapped to the library sequence with minimal edit distance. This was necessary because bwa-mem did not always correctly map paired reads as a pair, a problem most evident in the mutant library with many similar sequences. Pairwise Levenshtein edit distance was computed using the Python package editdistance 0.5.3.

Paired reads exceeding the edit distance threshold were discarded using reformat.sh from BBTools 38.61. Duplicate reads were identified and deduplicated using utmi_tools 1.0.0. Finally, reads mapped to each DNA library fragment sequence were counted.

Training Deep Learning Models to Predict Activation

Twenty percent (20%) of the total library sequences were reserved as a held-out test set and split the remaining library into 10 splits for cross-validation.

Two broad ways of encoding library peptide sequences were considered. For each encoding method, deep learning regression models were developed to predict activation from those encodings. All models were trained using mean squared error as the loss function.

The first category of encodings did not retain explicit position-specific information. As a specific method, each peptide was encoded as a 20-dimensional vector giving the proportions of each of the 20 amino acids. Using scikit-learn 0.22.1, fully-connected neural networks were trained with 1 to 20 hidden layers of width 20 and ReLU activation using either the Adam or SGD optimizer and the default initial learning rate of 0.001 and L2-penalty of 0.0001.

The second category of encodings explicitly retained position-specific information. For a library peptide sequence of length L, these encoding methods produced a L-by-d matrix, where d depended on the specific encoding method. The most expressive encoding was a one-hot encoding with d=20. Amino acid embeddings learned by the UniRep model (d=10) were also tried, and a d=2 embedding method capturing the charge (1 for lysine and arginine, −1 for aspartic acid and glutamic acid, 0 otherwise) and Wimley-White interfacial hydrophobicity of each amino acid. Using TensorFlow 2.2, convolutional neural networks were trained with 3-9 convolutional layers followed by max-pooling along either the channels or sequence-length dimension and 2 fully-connected layers of width 20. Kernel sizes between 5 and 20, channel widths (i.e., number of filters at each convolutional layer) between 10 and 20, L2 weight penalties between 1e-3 and 1e-5, and initial learning rates between 1e-2 and 1e-4 were tried experimentally. Batch norm and Swish or ReLU activation was applied to each convolutional and fully-connected layer (except the last layer). Models were trained using the Adam optimizer for up to 500 epochs with two scheduling callbacks: reduction of the learning rate by 5-fold if training loss did not improve for 20 epochs, and early stopping if no improvement on the validation loss was observed for 50 epochs. Models were trained on Stanford's Sherlock computing cluster using CPUs only. The final model had 9 convolutional layers of kernel size 10 and channel width 30 followed by max-pooling along the sequence dimension; swish activation was applied to each layer (except the last). This model was trained using the adam optimizer with batch normalization, an L2 weight penalty of 1e-3, a dropout of 0.1, and an initial learning rate of 1e-3.

Doctrine of Equivalents

Having described several embodiments, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Those skilled in the art will appreciate that the foregoing examples and descriptions of various preferred embodiments of the present invention are merely illustrative of the invention as a whole, and that variations in the components or steps of the present invention may be made within the spirit and scope of the invention. Accordingly, the present invention is not limited to the specific embodiments described herein, but, rather, is defined by the scope of the appended claims.

What is claimed is:

1. A method, comprising:
   obtaining a convolutional neural network (CNN), wherein the CNN is trained with nonrandom functional activation domain data from a first organism; and
   identifying an activation domain in a second organism using the CNN.

2. The method of claim 1, wherein the functional activation domains are described by at least one of: peptide sequence, predicted secondary structure, actual secondary structure, predicted disorder, and activity of the functional activation domain.

3. The method of claim 1, further comprising:
   obtaining the functional activation domain data; and
   training the CNN with the functional activation domain data.

4. The method of claim 3, wherein obtaining functional activation domain data comprises:
   obtaining a library of nucleic acid molecules, wherein each molecule in the library of nucleic acid molecules encodes a peptide comprising a DNA-binding domain and a potential activation domain;
   providing the library to a collection of cells, wherein each cell in the collection of cells includes a target gene operatively coupled to a promoter region to which the DNA-binding region binds;
   screening the collection of cells for a cell that expresses the target gene, which indicates a functional activation domain within the molecule from nucleic acid molecules provided to the cell; and
   identifying the functional activation domain in the library.

5. The method of claim 4, wherein identifying the functional domain comprises sequencing the nucleic acid molecule introduced into the cell.

6. The method of claim 4, further comprising screening the collection of cells for a cell that expresses the molecule from the library of nucleic acid molecules.

7. The method of claim 4, wherein the peptide further comprises a reporter domain.

8. The method of claim 7, wherein the reporter domain is selected from the group consisting of: mCherry, GFP, YFP, RFP, DsRed, mStrawberry, mOrange, and dTomato.

9. The method of claim 4, wherein screening the collection of cells for a cell that expresses the target gene simultaneously screens the collection of cells for a cell that expresses the molecule from the library of nucleic acid molecules.

10. The method of claim 4, wherein identifying the functional activation domain comprises sequencing the molecule from the library of nucleic acid molecules introduced to the cell.

11. The method of claim 4, wherein the peptide further comprises an inducer domain, and the method further comprises inducing expression of the target gene.

12. The method of claim 11, wherein inducing expression comprises providing an exogenous chemical to the collection of cells.

13. The method of claim 12, wherein the inducer is an estrogen inducer, and the exogenous chemical is estrogen.

14. The method of claim 4, wherein the collection of cells are selected from bacteria, yeast cells, plant cells, and mammalian cells.

15. The method of claim 4, wherein the collection of cells are yeast cells.

16. The method of claim 1, wherein the CNN possesses 1-20 hidden layers.

17. The method of claim 1, wherein the CNN possesses 3-9 convolutional layers.

18. The method of claim 1, wherein the CNN possesses 9 convolutional layers of kernel size 10 and channel width 30.

19. The method of claim 1, wherein the first organism and the second organism are different species.

20. The method of claim 1, further comprising:
   obtaining the functional activation domain data; and
   training the CNN with the functional activation domain data;
   wherein the CNN possess 1-20 hidden layers and 3-9 convolutional layers, wherein the convolutional layers possess kernel size 10 and channel width 30; and
   wherein the functional activation domains are described by at least one of: peptide sequence, predicted secondary structure, actual secondary structure, predicted disorder, and activity of the functional activation domain.

* * * * *

UNITED STATES PATENT AND TRADEMARK OFFICE
CERTIFICATE OF CORRECTION

| | | |
|---|---|---|
| PATENT NO. | : 11,732,381 B2 | Page 1 of 1 |
| APPLICATION NO. | : 17/300935 | |
| DATED | : August 22, 2023 | |
| INVENTOR(S) | : Roger D. Kornberg, Adrian Sanborn and Benjamin Yeh | |

It is certified that error appears in the above-identified patent and that said Letters Patent is hereby corrected as shown below:

In the Specification

In the STATEMENT REGARDING FEDERALLY SPONSORED RESEARCH OR DEVELOPMENT:
Column 1, Line 18: replace "This invention was made with Governmental support under Contract Nos. 133097 and 11696 awarded by the National Institutes if Health. The government has certain rights in this invention." with --This invention was made with Government support under contracts DK121366 and GM049985 awarded by the National Institutes of Health. The Government has certain rights in the invention.--

Signed and Sealed this
Fourth Day of November, 2025

John A. Squires
*Director of the United States Patent and Trademark Office*